United States Patent
Tegels

(10) Patent No.: US 8,647,365 B2
(45) Date of Patent: Feb. 11, 2014

(54) CARRIER TUBE FOR VASCULAR CLOSURE DEVICE AND METHODS

(75) Inventor: Zachary J. Tegels, Otsego, MN (US)

(73) Assignee: St. Jude Medical Puerto Rico LLC, Caguas, PR (US)

( * ) Notice: Subject to any disclaimer, the term of this patent is extended or adjusted under 35 U.S.C. 154(b) by 156 days.

(21) Appl. No.: 13/390,164

(22) PCT Filed: Aug. 9, 2010

(86) PCT No.: PCT/US2010/002192
§ 371 (c)(1),
(2), (4) Date: Feb. 13, 2012

(87) PCT Pub. No.: WO2011/019374
PCT Pub. Date: Feb. 17, 2011

(65) Prior Publication Data
US 2012/0143245 A1 Jun. 7, 2012

Related U.S. Application Data

(60) Provisional application No. 61/234,192, filed on Aug. 14, 2009.

(51) Int. Cl.
*A61B 17/08* (2006.01)
*A61D 1/00* (2006.01)

(52) U.S. Cl.
USPC ........................................................ 606/213

(58) Field of Classification Search
USPC .......... 606/213–215, 226, 232, 233, 138, 148
See application file for complete search history.

(56) References Cited

U.S. PATENT DOCUMENTS

| 5,179,963 | A | | 1/1993 | Berger | |
|---|---|---|---|---|---|
| 5,545,178 | A | * | 8/1996 | Kensey et al. | 606/213 |
| 5,649,959 | A | * | 7/1997 | Hannam et al. | 606/213 |
| 5,814,073 | A | * | 9/1998 | Bonutti | 606/232 |
| 5,935,147 | A | * | 8/1999 | Kensey et al. | 606/213 |
| 6,007,563 | A | * | 12/1999 | Nash et al. | 606/213 |
| 6,045,569 | A | * | 4/2000 | Kensey et al. | 606/213 |
| 6,077,276 | A | | 6/2000 | Kontos | |
| 6,090,130 | A | | 7/2000 | Nash et al. | |
| 6,179,863 | B1 | * | 1/2001 | Kensey et al. | 606/215 |
| 7,597,705 | B2 | * | 10/2009 | Forsberg et al. | 606/213 |

(Continued)

FOREIGN PATENT DOCUMENTS

| EP | 0637431 A1 | 2/1995 |
|---|---|---|
| WO | 9417738 A2 | 8/1994 |

OTHER PUBLICATIONS

PCT International Search Report for PCT International Patent Application No. PCT/US2010/002192 mailed Jan. 19, 2011.

*Primary Examiner* — Darwin Erezo
*Assistant Examiner* — Katrina Stransky
(74) *Attorney, Agent, or Firm* — Holland & Hart

(57) ABSTRACT

A vascular closure device (200) includes a carrier tube (202), an anchor (208), a sealing pad (210), and a suture (204). The carrier tube defines a first lumen (268) and comprises a distal portion (260) and a proximal portion (262). The carrier tube is insertable through an insertion sheath (216). The anchor is positioned outside of the carrier tube. The sealing pad is positioned inside the first lumen. The suture couples the sealing pad to the anchor. The distal portion of the carrier tube has a different material composition from the proximal portion.

20 Claims, 13 Drawing Sheets

(56) References Cited

U.S. PATENT DOCUMENTS

| | | | |
|---|---|---|---|
| 7,621,937 B2* | 11/2009 | Pipenhagen et al. | 606/232 |
| 8,382,795 B2* | 2/2013 | Forsberg et al. | 606/213 |
| 2005/0085851 A1 | 4/2005 | Fiehler et al. | |
| 2005/0096697 A1* | 5/2005 | Forsberg et al. | 606/213 |
| 2005/0125030 A1* | 6/2005 | Forsberg et al. | 606/213 |
| 2005/0125031 A1 | 6/2005 | Pipenhagen et al. | |
| 2005/0234396 A1* | 10/2005 | Forsberg et al. | 604/43 |
| 2006/0229674 A1 | 10/2006 | Forsberg | |
| 2006/0265006 A1 | 11/2006 | White et al. | |
| 2009/0163934 A1 | 6/2009 | Raschdorf, Jr. et al. | |
| 2009/0312790 A1* | 12/2009 | Forsberg et al. | 606/213 |

\* cited by examiner

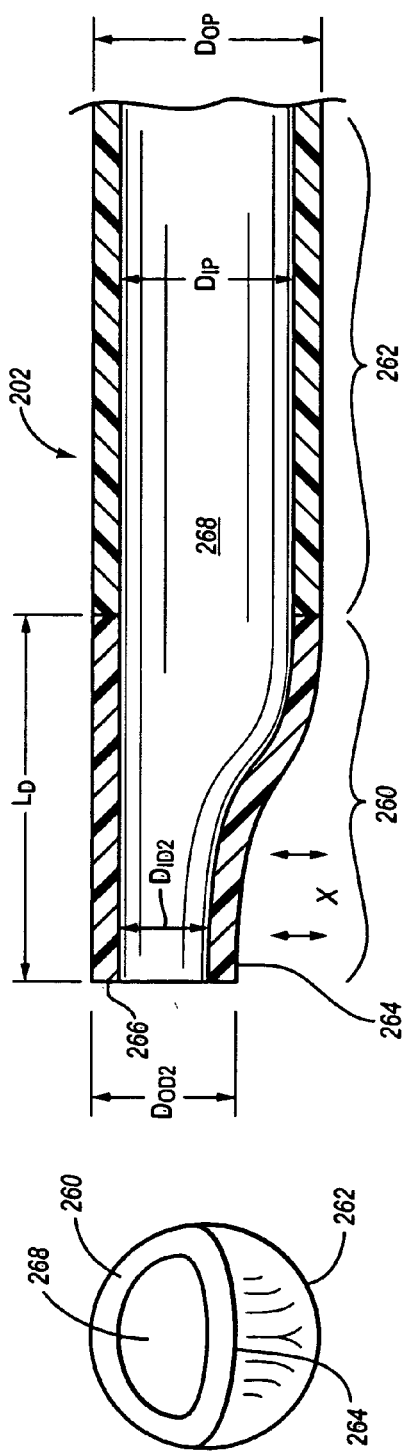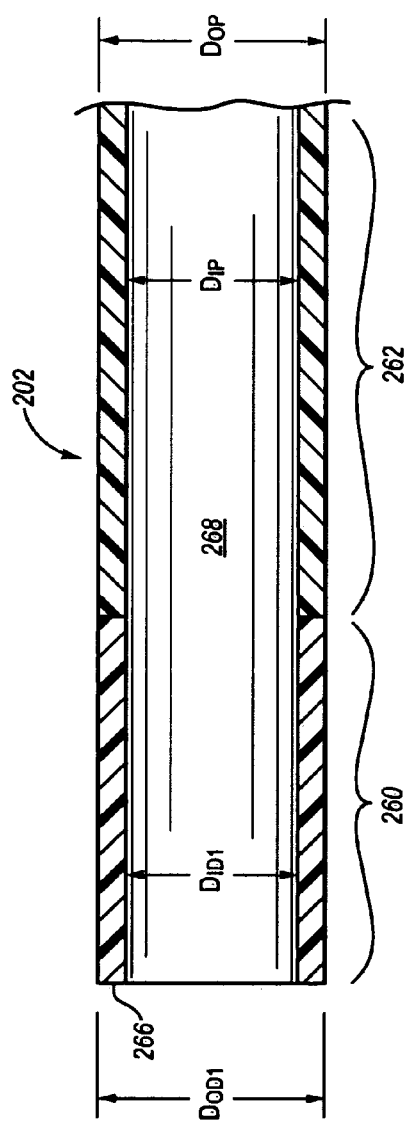
Fig. 6
Fig. 5
Fig. 6A

CARRIER TUBE FOR VASCULAR CLOSURE DEVICE AND METHODS

RELATED APPLICATION

This application claims the benefit of U.S. Provisional Patent Application No. 61/234,192, filed Aug. 14, 2009, which is hereby incorporated by reference herein in its entirety.

TECHNICAL FIELD

The present disclosure relates generally to medical devices and more particularly to vascular closure devices.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices, such as those described in U.S. Pat. Nos. 6,090,130 and 6,045,569, which are hereby incorporated in their entireties by this reference.

Prior closure devices, such as the ones described in the above-mentioned patents, place an anchor inside the vessel to provide a backstop against which a sealing member that is positioned outside the vessel may be compressed. In some instances, a particular shaped insertion sheath is used to help position the anchor within the vessel and limit shuttling (return movement) of the anchor back into the insertion sheath. This insertion sheath may be structured different from the insertion sheath that is used for procedures related to treating the patient prior to sealing closed the vessel puncture with the vascular closure device. Requiring a sheath exchange as part of sealing closed the vessel puncture has many disadvantages.

SUMMARY

One aspect of the present disclosure relates to a vascular closure device that includes a carrier tube, an anchor, a sealing pad, and a suture. The carrier tube defines a first lumen and comprises a distal portion and a proximal portion. The distal portion has a different material composition from the proximal portion. The carrier tube is insertable through an insertion sheath. The anchor is positioned outside of the carrier tube. The sealing pad is positioned inside the first lumen. The suture couples the sealing pad to the anchor.

The distal portion of the carrier tube may have at least one of a greater flexibility, a greater deformability, and a greater compressibility than the proximal portion of the carrier tube. The distal portion may include at least one of a thermoplastic polyurethane material, a thermoplastic polyethylene material, a hydrogel material, and a shape memory polymer. The hydrogel material may be an electroactive polymer (EAP). A portion of the anchor may be arranged adjacent to a peripheral outer surface of the distal portion of the carrier tube. The distal portion of the carrier tube may be movable between a deformed positioned and a rest position, wherein the deformed position defines a recess within which a portion of the anchor is positioned. The distal portion may be configured to maintain the deformed position while positioned in the insertion sheath. The distal portion may be configured to automatically move from the deformed position to the rest position after removal from the insertion sheath to limit return movement of the anchor into the insertion sheath. The carrier tube may define a second lumen arranged coaxial with the first lumen. The second lumen may be configured and arranged as a blood flow channel from the distal portion to the proximal portion of the carrier tube. The carrier tube may define a second lumen arranged parallel with and radially spaced apart from the first lumen. The second lumen may be configured and arranged as a blood flow channel from the distal portion to the proximal portion of the carrier tube. The distal portion may comprise a lubricious component.

Another aspect of the present disclosure relates to a vascular closure system that includes an insertion sheath and a vascular closure device. The insertion sheath includes a distal end and is configured for insertion through a vessel puncture. The vascular closure device includes a carrier tube, an anchor, and a sealing pad. The carrier tube has a proximal portion and a distal portion. The distal portion is elastically deformable to define an recess along an outer surface thereof. The carrier tube is positionable within the insertion sheath. The anchor has at least a portion thereof positioned in the recess while the distal portion of the carrier tube is positioned in the insertion sheath. The sealing pad is positioned in the carrier tube and coupled to the anchor with a suture. The distal portion automatically returns to an undeformed state to eliminate the recess when the distal portion of the carrier tube extends beyond the distal end of the insertion sheath.

The distal portion may comprise a different material composition than the proximal portion. The distal portion may have a different material thickness than a material thickness of the proximal portion. The distal portion may have a different flexibility property than the proximal portion. The distal portion may have a different compressibility property than the proximal portion. The distal portion may have a different deformability property than the proximal portion. The distal portion may include a shape memory material. The insertion sheath may maintain a constant shape and size during use with the vascular closure device.

A further aspect of the present disclosure relates to a method of treating a patient through a tissue puncture. The method includes providing an insertion sheath and a closure device, wherein the closure device includes an anchor, a sealing pad, and a carrier tube. The carrier tube includes a distal portion that is deformable to define a recess along an outer surface thereof. A portion of the anchor is positioned in the recess, and the sealing pad is positioned within the carrier tube. The method also includes inserting the insertion sheath through the tissue puncture, inserting a treatment instrument through the insertion sheath to treat the patient at a location distal of the insertion sheath, withdrawing the treatment instrument from the insertion sheath, inserting the carrier tube and anchor through the insertion sheath to a location distal of the insertion sheath, removing the anchor from the recess, automatically returning the distal portion of the carrier tube to an undeformed position, and sealing closed the tissue puncture with the vascular closure device.

The method may further include rotating the anchor to a position perpendicular to a longitudinal axis of the carrier tube. The method may include contacting the anchor against a distal end surface of the carrier tube. The method may include disposing the sealing pad on a proximal side of the tissue puncture and cinching the sealing pad to the anchor with a suture.

Another aspect of the present disclosure relates to a method of manufacturing a carrier tube for use with a vascular closure device. The method includes providing a distal carrier tube portion and a proximal carrier tube portion, wherein the distal carrier tube portion defines a distal lumen and is elastically deformable to define a recess along an exterior surface thereof. The proximal portion includes a proximal lumen. The method includes coaxially aligning the distal and proximal lumens, and providing the distal and proximal portions as a single piece structure.

Providing the distal and proximal portions as a single piece structure may include connecting the distal and proximal portions together using one of seamless extrusion, thermal bonding, ultrasonic welding, and adhesive. Thermal bonding may include at least one of hot jaw bonding, infrared (IR) welding, radio frequency (RF) welding, and diode laser bonding. The carrier tube may include a blood flow channel arranged in parallel with the distal and proximal lumens, and the method further comprises coaxially aligning a portion of the blood flow channel defined in the distal portion with a portion of the blood flow channel defined in the proximal portion prior to providing the distal and proximal portions as a single piece structure.

Additional advantages and novel features will be set forth in the description which follows or can be learned by those skilled in the art through reading these materials or practicing the examples disclosed herein. The advantages of the invention can be achieved through the means recited in the attached claims.

BRIEF DESCRIPTION OF THE DRAWINGS

The accompanying drawings illustrate various embodiments of the present disclosure and are a part of the specification. The illustrated embodiments are merely examples and do not limit the scope of the present disclosure.

FIG. 5 is a cross-sectional side view of a portion of an example carrier tube for use with a vascular closure device in accordance with the present disclosure.

FIG. 6 is a cross-sectional side view of the carrier tube of FIG. 5 with a distal portion thereof deformed to create a recess.

FIG. 6A is an end view of the carrier tube of FIG. 6.

Throughout the drawings, identical reference numbers designate similar, but not necessarily identical, elements.

DETAILED DESCRIPTION

Figure 1:
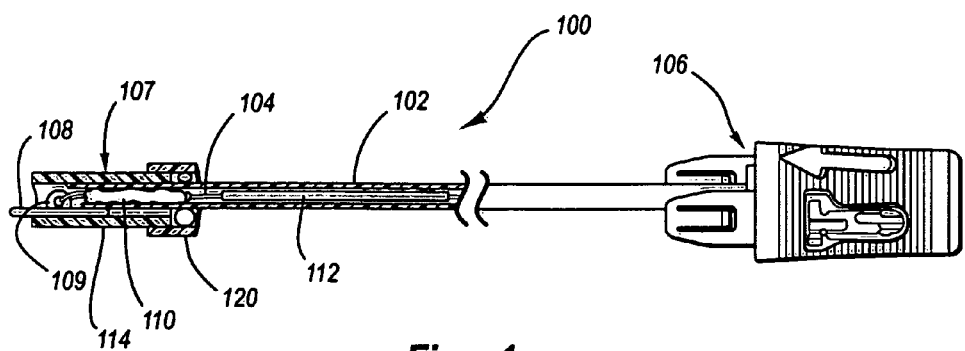
FIG. 1 is a side view of an example vascular closure device according to the present disclosure.

As mentioned above, vascular procedures are conducted throughout the world and require access to a vessel through a puncture. Often, the vessel is a femoral artery. To close the puncture following completion of the procedure, many times a closure device is used to sandwich the puncture between an anchor and a sealing pad. A suture may be used to couple together the anchor and sealing pad. A force may be applied along the suture to draw the anchor and sealing pad toward each other as the sealing pad is compressed against the puncture. Typically, the suture is manually cut at a location outside of the patient after confirmation that the puncture has been sealed.

The anchor is usually intended to remain in the vessel (intraluminal) at least while the puncture in the vessel is sealed closed. Some insertion sheaths used with such vascular closure devices include a monofold structure at a distal end of the insertion sheath. The monofold structure provides an obstruction to return passage of the anchor member into the insertion sheath after the anchor has been deployed distally from the insertion sheath. The distal end of the insertion sheath, due in part to the monofold structure, may provide a surface against which the anchor engages to rotate the anchor into a position generally parallel with the internal wall of the vessel. The anchor may then anchor against the vessel wall when the insertion sheath is retracted from the puncture.

A sheath exchange after treatment of the patient and prior to using the vascular closure device is typically required due to the differences between procedural insertion sheaths that are used with patient treatment instruments and closure insertions sheaths with monofold structures that are used with vascular closure devices. Sheath exchanges have several potential disadvantages and are avoided if possible. A sheath exchange typically requires two different sheaths, one being exchanged for the other, which results in higher equipment costs, greater complexity in the procedure, and increased time requirement for completion of the procedure. A sheath exchanges may also result in increased risk of damaging the patient or introducing infection at the treatment site.

The present disclosure is directed to a vascular closure device that includes a carrier tube with features that effectively eliminate the need for a sheath exchange. Alternatively, the vascular closure device of the present disclosure may be used with a closure insertion sheath that may or may not include a monofold structure. The carrier tube may include a deformable distal portion that provides nesting of the anchor along an outer surface of the carrier tube within the insertion sheath prior to deployment of the anchor. The distal portion of the carrier tube may recoil to an undeformed position after deployment of the anchor to a configuration that limits return (i.e., shuttling) of the anchor back into the insertion sheath. The carrier tubes of the present disclosure permit the same insertion sheath that is used for treatment of the patient to be used with a vascular closure device having an intraluminal positioned anchor to seal closed the vessel puncture.

The general structure and function of vascular closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

As used in this specification and the appended claims, the term "compact" or "compacting" is used broadly to mean any type of tamping (i.e., packing down by one or a succession of blows or taps or smooth, steady pressure, but not by excessive force), compacting, or compressing. "Engage" and "engageable" are also used broadly to mean interlock, mesh, or contact between two structures or devices. Likewise "disengage" or "disengageable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as used in the specification, including the claims, have the same meaning as the word "comprising."

Referring to FIGS. 1-4, a vascular puncture closure device 100 is shown according to the prior art. Some example closure devices in addition to closure device 100 that may be suited for use with the inventive principles described herein are disclosed in U.S. Published Patent Application Nos. 2005/0085851, 2006/0265006 and 2006/0229674, which applications are hereby incorporated in their entireties by this reference.

The vascular puncture closure device 100 includes a carrier tube 102 with a filament or suture 104 extending at least partially therethrough. The closure device 100 also includes a first or proximal end 106 and a second or distal end 107. External to a second or distal end 107 of the carrier tube 102 is an anchor 108. The anchor is an elongated, stiff, low profile member including an eye 109 formed at the middle. The anchor 108 is typically made of a biologically resorbable polymer.

The suture 104 is threaded through the anchor 108 and back to a collagen pad 110. The collagen pad 110 may be comprised of randomly oriented fibrous material bound together by chemical means. The collagen pad 110 is slidingly attached to the suture 104 as the suture passes distally through the carrier tube 102, but as the suture traverses the anchor 108 and reenters the carrier tube 102, it is securely slip knotted proximal to the collagen pad 110 to facilitate cinching of the collagen pad 110 when the closure device 100 is properly placed and the anchor 108 deployed (see FIG. 4).

The carrier tube 102 typically includes a compaction tube 112 disposed therein. The compaction tube 112 is slidingly mounted on the suture 104 and may be used by an operator to compact the collagen pad 110 toward the anchor 108 at an appropriate time to seal a percutaneous tissue puncture.

Prior to deployment of the anchor 108 within an vessel, the eye 109 of the anchor 108 rests outside the distal end 107 of the carrier tube 102. The anchor 108 may be temporarily held in place flush with the carrier tube 102 by a bypass tube 114 disposed over the distal end 107 of the carrier tube 102.

Figure 2:
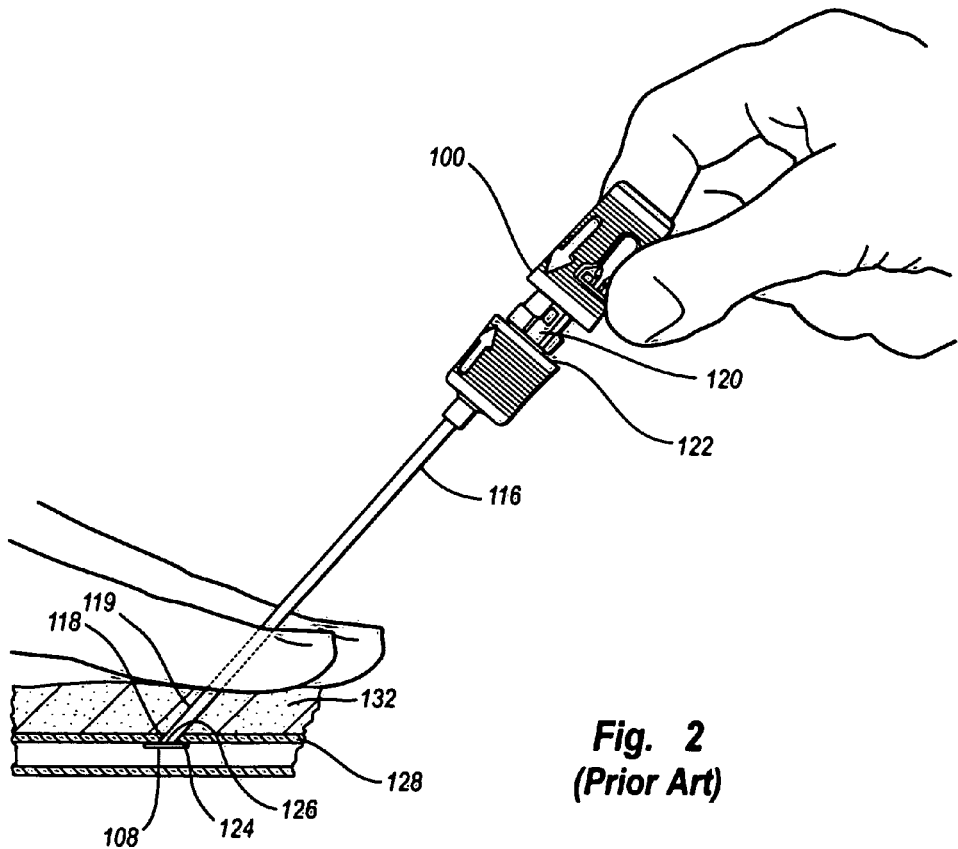
FIG. 2 is a side view of the vascular closure device shown in FIG. 1 with an anchor disposed in a vessel.
Figure 3:
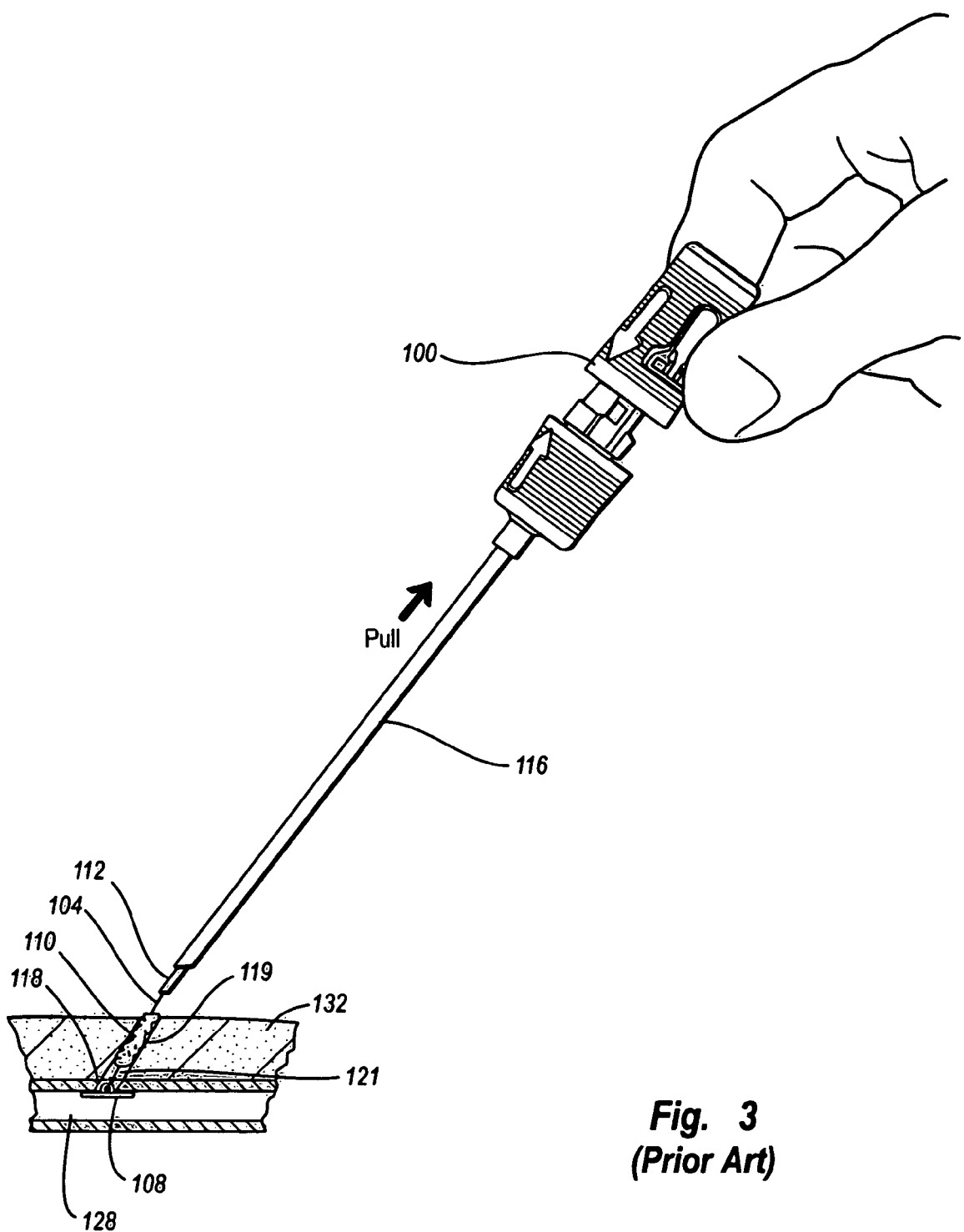
FIG. 3 is a side view of the vascular closure device shown in FIG. 1. with the sealing pad disposed in the percutaneous incision.
Figure 4:
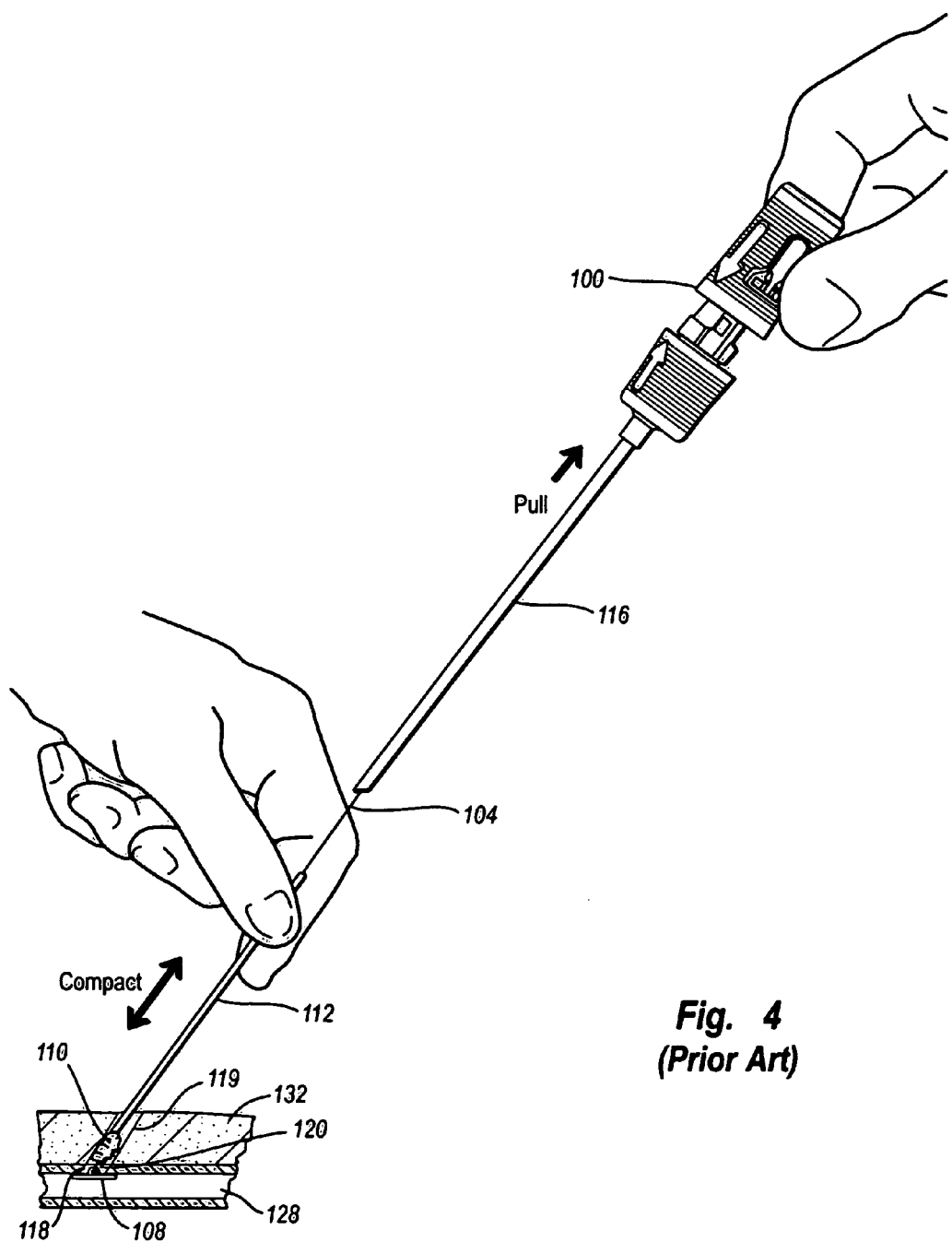
FIG. 4 is a side view of the vascular closure device shown in FIG. 1 with the sealing pad being compacted with a compaction member.

The flush arrangement of the anchor 108 and carrier tube 102 allows the anchor 108 to be inserted into a procedure sheath such as insertion sheath 116 as shown in FIGS. 2-4, and eventually through an arterial puncture 118. The insertion sheath 116 is shown in FIGS. 2-4 inserted through a percutaneous incision 119 formed in a tissue layer 132 and into an vessel 128. However, the bypass tube 114 (see FIG. 1) includes an oversized head 120 that prevents the bypass tube 114 from passing through an internal passage of the insertion sheath 116. Therefore, as the puncture closure device 100 is inserted into the insertion sheath 116, the oversized head 120 bears against a proximal surface 122 of insertion sheath 116.

Further insertion of the puncture closure device 100 results in sliding movement between the carrier tube 102 and the bypass tube 114, and releases the anchor 108 from the bypass tube 114 (see FIG. 1). However, the anchor 108 remains in the flush arrangement shown in FIG. 1 following release from the bypass tube 114, limited in movement by the insertion sheath 116.

The insertion sheath 116 typically includes a monofold 124 at a second or distal end 126 thereof. As discussed above, the insertion sheath 116 is exchanged with a procedural sheath, which was used to treat the patient prior using the closure device 100, in order to have the monofold 124 available. The monofold 124 acts as a one-way valve to the anchor 108. The monofold 124 is a plastic deformation in a portion of the insertion sheath 116 that elastically flexes as the anchor 108 is pushed out through the distal end 126 of the insertion sheath 116. Typically, after the anchor 108 passes through the distal end 126 of the insertion sheath 116 and enters the vessel 128, the anchor 108 is no longer constrained to the flush arrangement with respect to the carrier tube 102 and it deploys and rotates to the position shown in FIG. 2.

Referring next to FIGS. 3-4, with the anchor 108 deployed, the puncture closure device 100 and the insertion sheath 116 are withdrawn together, ejecting the collagen pad 110 from the carrier tube 102 into the incision tract 119 and exposing the compaction tube 112. With the compaction tube 112 fully exposed as shown in FIG. 4, the collagen pad 110 is manually compacted, and the anchor 108 and collagen pad 110 are cinched together and held in place with the self-tightening slip-knot on the suture 102. Thus, the tissue puncture is sandwiched between the anchor 108 and the collagen pad 110, thereby sealing the tissue puncture 118. The suture 104 is then cut and the incision tract 119 may be closed. The suture 104, anchor 108, and collagen pad 110 are generally made of resorbable materials and therefore remain in place while the puncture 118 heals.

It may be difficult to eject and compact of the collagen pad 110 using the typical tissue puncture closure device 100 described above. The monofold 124 of the insertion sheath 116 resists deformation as the collagen pad 110 is ejected from the carrier tube and compacting cannot commence until the sheath 116 and carrier tube 102 have been removed so as to expose the compaction tube 112 for manual grasping. Under certain conditions, removal of the sheath 116 prior to compacting the collagen pad 110 causes the collagen pad 110 to retract or displace proximally from the tissue puncture 118, creating an undesirable gap 121 between the collagen pad 110 and the puncture 118. The gap 121 may remain even after compacting as shown in FIG. 4, and sometimes results in only a partial seal and bleeding from the tissue puncture 118.

Referring now to FIGS. 5 and 6, an example carrier tube 202 for use with a vascular closure device (e.g., vascular closure device 200 shown in FIG. 12) is shown and described. The carrier tube 202 includes a distal portion 260 and a proximal portion 262. The distal portion 260 may be deformable to provide a recess feature 264 (see FIG. 6). The distal portion 260 may comprise an elastic construction that provides creation of the recess 264 by temporary movement of a portion of the distal portion 260 in a radial direction X from the rest state (also referred to as an undeformed state or position) shown in FIG. 5 to the deformed state shown in FIG. 6 followed by return to the rest state shown in FIG. 5.

In the rest state of FIG. 5, the distal portion 260 has an inner dimension $D_{ID1}$ and an outer dimension $D_{OD1}$, and the proximal portion 262 has an inner dimension $D_{IP}$ and an outer dimension $D_{OP}$. In the deformed state shown in FIG. 6, the recess 264 defines a minimum inner dimension $D_{ID2}$ and a minimum outer dimension $D_{OD2}$ at the distal portion 260, while the proximal portion 262 typically maintains the inner dimension $D_{IP}$ and outer dimension $D_{OP}$. A depth of the recess 264 (i.e., the difference between $D_{OD1}$ and $D_{OD2}$) is typically at least as great as a thickness of that portion of the anchor of the vascular closure device that is positioned within the recess 264. The recess 264 may extend along an entire length $L_D$ of the distal portion 260. In other arrangements, the total length $L_D$ of the distal portion 260 may be substantially greater than a length of the recess 264. The recess 264 may extend to a distal surface 266 of the carrier tube 202. The depth of the recess 264 may be greatest at the distal end surface 266.

The carrier tube 202 may define a carrier tube lumen 268. The lumen 268 is typically sized to retain a sealing pad. The sealing pad is typically carried by the carrier tube 202 to the vessel puncture where the sealing pad is disposed for sealing the vessel puncture. In some arrangements, the sealing pad extends into the distal portion 260 of the carrier tube 202. The sealing pad may extend into a position within lumen 268 that is radially adjacent to the recess 264. In other arrangements, the sealing pad remains positioned proximal of the recess 264.

Various constructions and configurations for the recess 264 are possible. Some examples of recess constructions are shown and described in U.S. Published Application No. 205/0125031, which is hereby incorporated in its entirety by this reference. The recess feature of the present disclosure is temporarily defined in the carrier tube rather than being permanently defined in the carrier tube as disclosed in, for example, U.S. Published Application No. 2005/0125031.

The distal and proximal portions 260, 262 may comprise different physical properties. In at least one example, the distal portion 260 has a greater flexibility property than the proximal portion 262. In at least one example, the distal portion 260 has at least one of a greater compressibility property and a greater deformability property than the proximal portion 262. The increased flexibility, compressibility, and/or deformability property of the distal portion 260 may provide the ability to deform the distal portion 260 to create the recess 264 and to recoil the distal portion 260 to change from the deformed state shown in FIG. 6 to the rest or undeformed state shown in FIG. 5. The proximal portion 262 may maintain a more rigid, less flexible construction that promotes improved control when inserting the carrier tube 202 into an insertion sheath and transferring axial forces along the length of the carrier tube to advance and retract the carrier tube relative to the insertion sheath.

The distal portion 260 may comprise any one or a combination of materials that provide elastic deformability of the distal portion 260. Some example materials include thermoplastic elastomers, for example, thermoplastic polyurethane elastomers (e.g., Tecothane® and Pellethane®), low durometer polyether block amides (e.g., PEBAX®'s), and low durometer polyamides (nylons) (e.g., GRILAMID®'s), to name a few. Shape memory polymers can also be used, for example, thermoplastic polyethylenes, poly(methyl methcrylate) (PMMA), polyethylene terepthalate (PET), methyl methacrylate/acrylic acid copolymers (MMA/AA), polytetrafluoroethylene (PTFE), poly-L-lactide (PLLA), poly(glycolic acid) (PGA), polynorbene, oligo (e-caprolactone), hydrogels, and polyethylene terepthalate-polyethylene oxide block copolymers (PET-PEO), to name just a few. The polyurethanes can include polyurethanes with ionic or mesogenic components. Other such shape memory polymers are contemplated. The hydrogel may include an electroactive polymer (EAP). The electroactive polymer may be activated by an electronic stimulus that changes a shape of the object when the EAP is activated by the electronic stimulus. Additionally, shape memory alloys can also be used, for example, nitinol, Elgiloy® cobalt-chromium-nickel alloy, Tinel® nickel-titanium alloy, copper-aluminum-nickel alloys, and copper-zinc-aluminum alloys, to name a few. Silicone can also be used in the distal portion 260.

The carrier tube 202, in particular the distal portion 260 of the carrier tube 202, may comprise a lubricious material. In one example, the lubricious material includes graphite. The lubricious material may be included as an integral part of the material composition of the carrier tube 202. Alternatively, the lubricious material may be added as a coating on one or more surfaces of the carrier tube (i.e., the inner or outer surface). Providing the carrier tube with a lubricious material may improve ejection of the sealing pad from within the carrier tube. The lubricious material may also improve ease of advancing a compaction tube within the carrier tube or advancing the carrier tube within the insertion sheath. A carrier tube that includes a lubricious material may also accelerate removal of the anchor from within the recess 264. Other examples of the lubricious materials for use with the carrier tube include, for example, polytetrafluoroethylene (PTFE), Molybdenum disulfide, and tungsten disulfide.

The distal and proximal portions 260, 262 may be constructed using various manufacturing techniques. In one example, the distal and proximal portions 260, 262 are constructed as separate pieces that are later connected together. Some example techniques for connecting two separate pieces include, for example, thermal processes such as hot jaw heating, infrared (IR) heating, and radio frequency (RF) heating and/or welding. Other connecting techniques include, for example, ultrasonic welding, diode laser welding, and adhesives. Alternatively, the distal and proximal portions 260, 262 may be created using a seamless extrusion process, co-molding, or other integral formation processes.

A process of creating the carrier tube 202 may include separately forming the distal and proximal portions 260, 262, coaxially aligning the distal and proximal portions 260, 262, and connecting the distal and proximal portions 260, 262 using, for example, one of the connecting or bonding techniques described above. Another example method of creating the carrier tube 202 may include, for example, extruding one of the distal and proximal portions 260, 262 followed by seamlessly extruding the other of the distal and proximal portions 260, 262.

In some example methods of sealing closed a vessel puncture, the intraluminally placed anchor is rotated into position generally perpendicular to a longitudinal axis of the carrier tube by contact between the anchor and a distal end surface of the insertion sheath (i.e., see FIG. 2). Using the insertion sheath to rotate the anchor into a position (i.e., the perpendicular position described above), wherein the anchor contacts against the inner side wall of the vessel, presents the opportunity for the anchor to shuttle back into the interior of the insertion sheath. As described above, an insertion sheath with a monofold structure is typically used with intraluminally placed anchors so as to limit the chance of shuttling of the anchor back into the insertion sheath. An alternative to using the insertion sheath to rotate the anchor is to use the distal end of the carrier tube to rotate the anchor into position. Typically, the carrier tube has an inner dimension (even in the rest state shown in FIG. 5) that is substantially less than the inner dimension of the insertion sheath. Thus, the carrier tube inherently provides a greater restriction for shuttling of the anchor back into the carrier tube before or after the anchor is rotated into the perpendicular orientation noted above. Positioning the distal end surface of the carrier tube flush with the distal end surface of the insertion sheath, at a location extending distally from the distal end of the insertion sheath, or just proximal of the distal end of the insertion sheath may limit if not eliminate the ability of the anchor to shuttle back into the insertion sheath.

Figure 7:
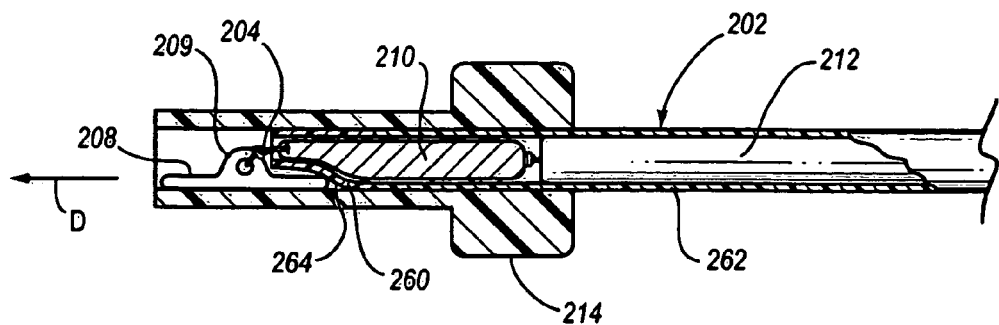
FIG. 7 is a cross-sectional side view of a distal end portion of a vascular closure device prior to insertion into an insertion sheath.
Figure 8:
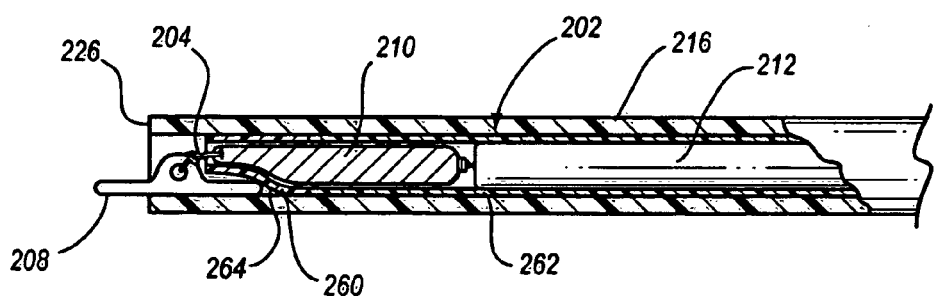
FIG. 8 is a cross-sectional side view of the distal end portion of the vascular closure device of FIG. 7 inserted into an insertion sheath.
Figure 9:
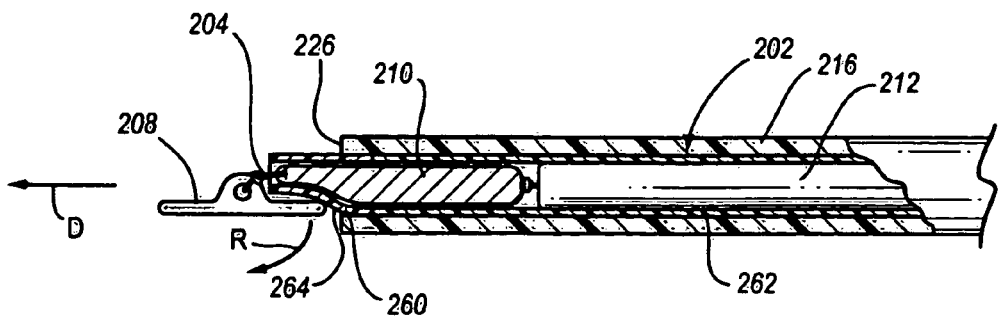
FIG. 9 is a cross-sectional side view of the vascular closure device and insertion sheath of FIG. 8 with the anchor advanced distally out of the insertion sheath.

Referring now to FIGS. 7-11, one example use of the carrier tube 202 is to position the anchor at a rotated position while limiting shuttling of the anchor back into the insertion sheath as described. Referring first to FIG. 7, the distal portion 260 of the carrier tube is deformed to create a recess 264. A portion of the anchor 208 is positioned within the recess at a location radially adjacent to that portion of the carrier tube 202 that defines the recess 264. A portion of the anchor 208 may be positioned adjacent to a peripheral outer surface of the carrier tube 202. A portion of the anchor 208 may be positioned radially outward from an outer circumferential surface of the carrier tube 202, such as a radially outward facing surface of the recess 264 along the distal portion 260.

The anchor 208 and distal portion 260 of the carrier tube 202 are positioned within a bypass tube 214. The bypass tube 214 retains the anchor 208 within the recess 264 and maintains the distal portion 260 in the deformed state. A sealing pad 210 may be positioned within the carrier tube. A compaction tube 212 may also be positioned within the carrier tube at a location proximal of the sealing pad 210. A suture 204 connects the anchor 208 to the sealing pad 210. The suture 204 may also extend proximally through the sealing pad 210 and the compaction tube 212 to a proximal location on a vascular closure device on which the carrier tube 202 is a part.

Figure 10:
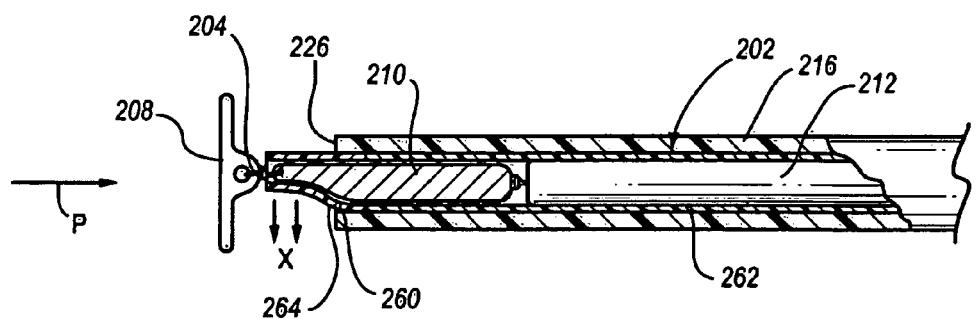
FIG. 10 is a cross-sectional side view of the vascular closure device and insertion sheath of FIG. 9 with the anchor rotated.
Figure 11:
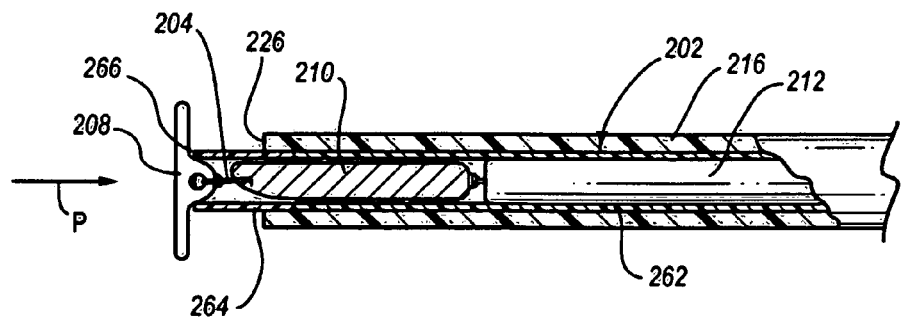
FIG. 11 is a cross-section side view of the vascular closure device and insertion sheath of FIG. 10 with the carrier tube distal end portion recoiled to a rest state to remove the recess feature.

The bypass tube 214 is inserted into a proximal opening of an insertion sheath 216. The bypass tube 214 maintains a fixed or stopped position in the insertion sheath while the compaction tube 212 continues to advance through the carrier tube to a position shown in FIG. 8. Typically, the insertion sheath 216 is positioned extending through a vessel puncture with the distal end surface 226 positioned within the vessel. The carrier tube 202 with anchor 208 is advanced further distally until reaching the position shown in FIG. 9 in which the entirety of the anchor 208 is positioned distal of the distal end surface 226 of the insertion sheath 216. The anchor 208 then rotates in the direction R and the distal portion 260 of the carrier tube 202 recoils in the radial direction X as shown in FIG. 10. The recoiling action of the distal portion 260 may help to rotate the anchor 208 in the direction R. In other instances, rotation of the anchor 208 in the direction R permits the distal portion 260 to recoil in the radial direction X.

Tension may be applied to the suture 204 that drives the anchor 208 (i.e., in particular an eye portion 209 of the anchor 208) against the distal end surface 266 of the carrier tube 202. Typically, the anchor 208 is positioned generally perpendicular to a longitudinal axis of the carrier tube 202, or at least in a rotated position in the direction R sufficient to promote anchoring and locating of the anchor 208 against an inner surface of the vessel adjacent to the vessel puncture.

In at least some arrangements, the outer diameter or maximum outer dimension of the carrier tube (i.e., $D_{OD1}$ and $D_{OP}$) is similar in size to the minimum internal dimension of the insertion sheath 216. The inner dimension of the carrier tube in the rest state ($D_{ID1}$) and in the deformed state ($D_{ID2}$) at the distal portion 260 is typically smaller than the maximum dimension of an end of the anchor. Further, the sealing pad 210 is typically positioned within the carrier tube adjacent to the distal end 266 to block passage of objects proximally into the carrier tube 202. As a result, when the distal portion 260 recoils in the direction X to the rest or undeformed position shown in FIG. 11, it would be difficult for the anchor 208 to shuttle back into the insertion sheath in a space defined between the outer surface of the carrier tube 202 and the inner surface of the insertion sheath 216. Furthermore, the inner dimension of the carrier tube 202 is sized such that it would typically be difficult for the anchor 208 to shuttle into the interior of the carrier tube 202, particularly when tension is applied to the suture that drives the center portion of the anchor towards the interior of the carrier tube 202 (i.e., the eye 209) as opposed to one of the free ends of the anchor 208.

Referring now to FIGS. 12-18, an example method of sealing a vessel puncture using a vascular closure device 200 and a procedural sheath 216 is shown and described. As noted above, the procedural sheath 216 does not include a monofold structure as is typically required for insertion sheaths that are used with a closure device having an intraluminal anchor.

Figure 12:
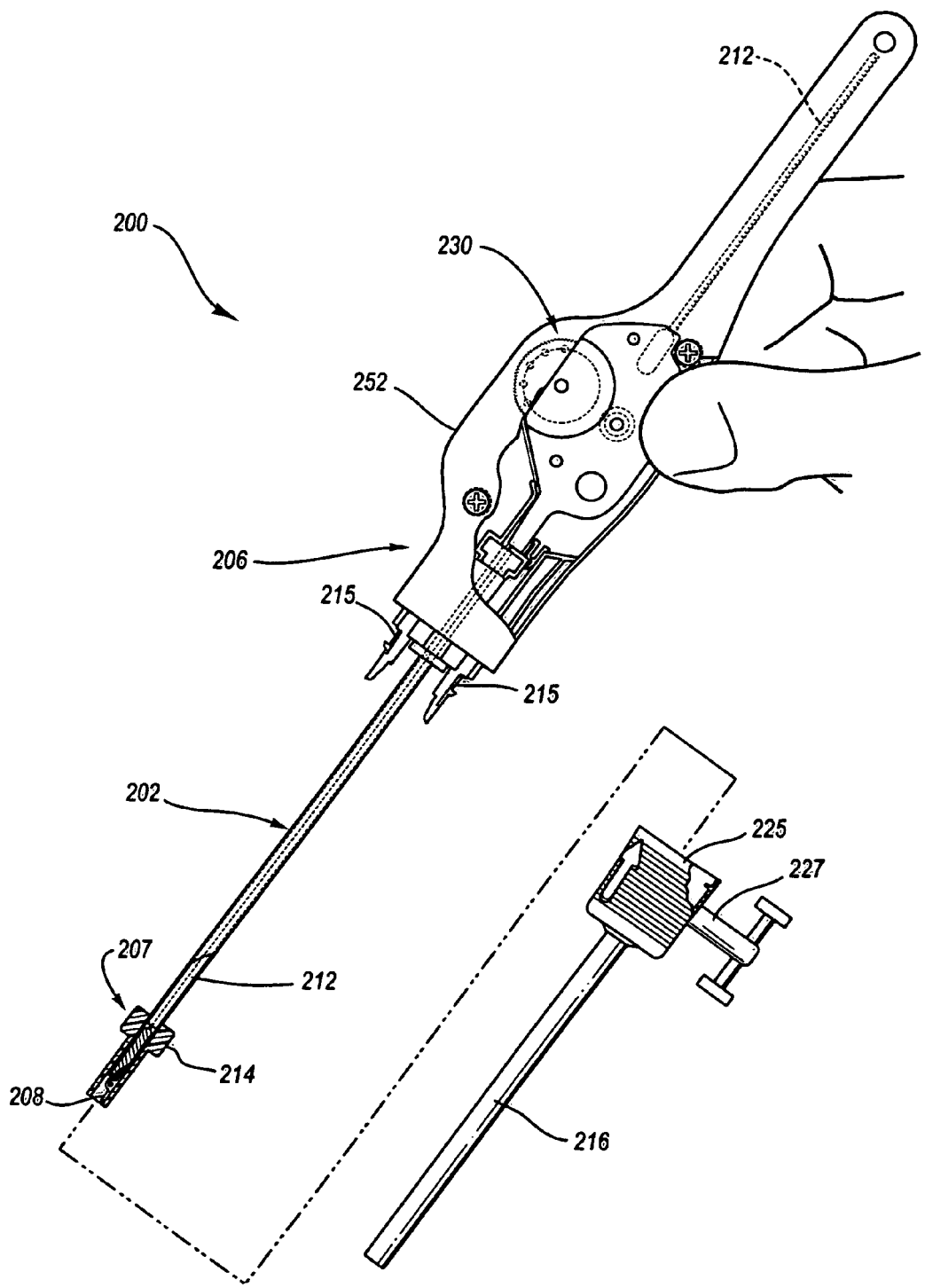
FIG. 12 is a side view of an example vascular closure device and insertion sheath in accordance with the present disclosure.
Figure 13:
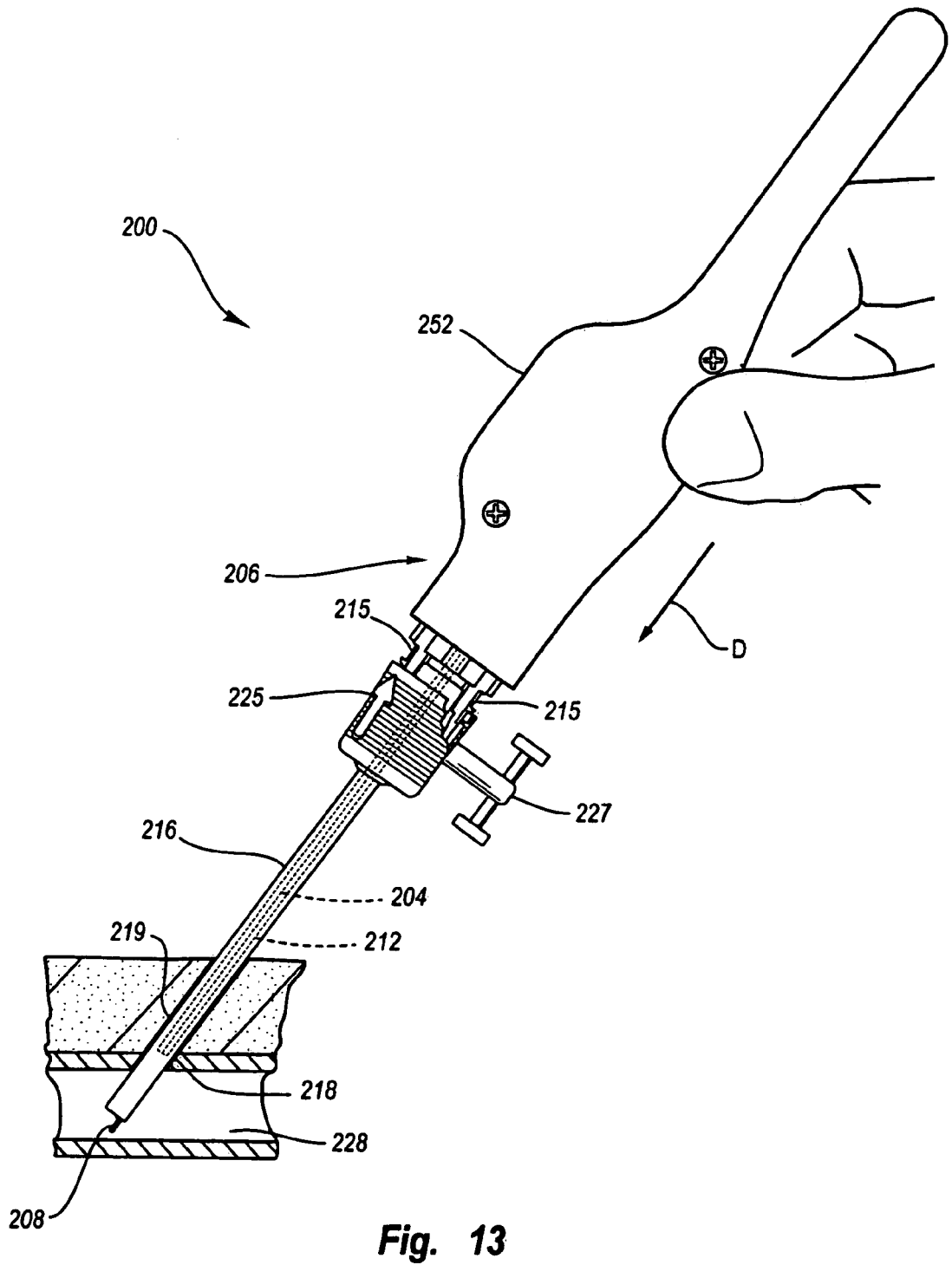
FIG. 13 is a side view of the vascular closure device and insertion sheath of FIG. 12 inserted into a tissue puncture.

Referring to FIG. 12, the vascular closure device 200 includes a carrier tube 202, a suture 204 that extends from a proximal end 206 to a distal end 207, an anchor 208 having an eye 209, a sealing pad 210, a compaction tube 212 and a bypass tube 214. Typically, a distal end of the insertion sheath is positioned extending through a percutaneous incision 219 and vascular puncture 218 into a vessel 228 as shown in FIG. 13. The bypass tube 214 is inserted into a proximal end of the insertion sheath 216 at a hub 225. The hub 225 may include a plurality of side ports 227 extending therefrom. The carrier tube 202 with anchor 208 are advanced distally in the direction D shown in FIG. 13 until the connecting arms 215 of the vascular closure device 200 connect with the hub 225.

Figure 14:
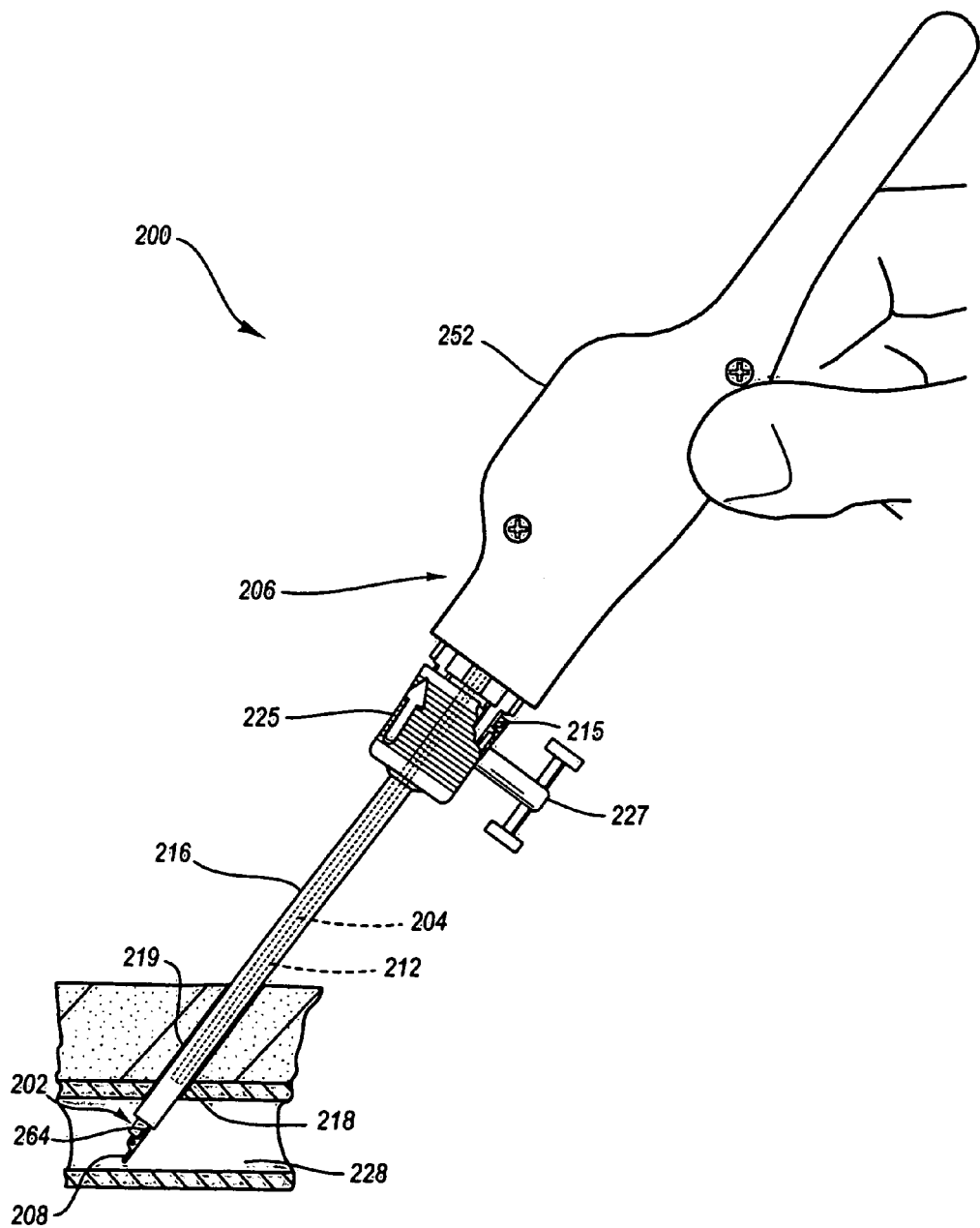
FIG. 14 is a side view of the vascular closure device and insertion sheath of FIG. 13 with an anchor member advanced distally from the insertion sheath.
Figures 15, 16:
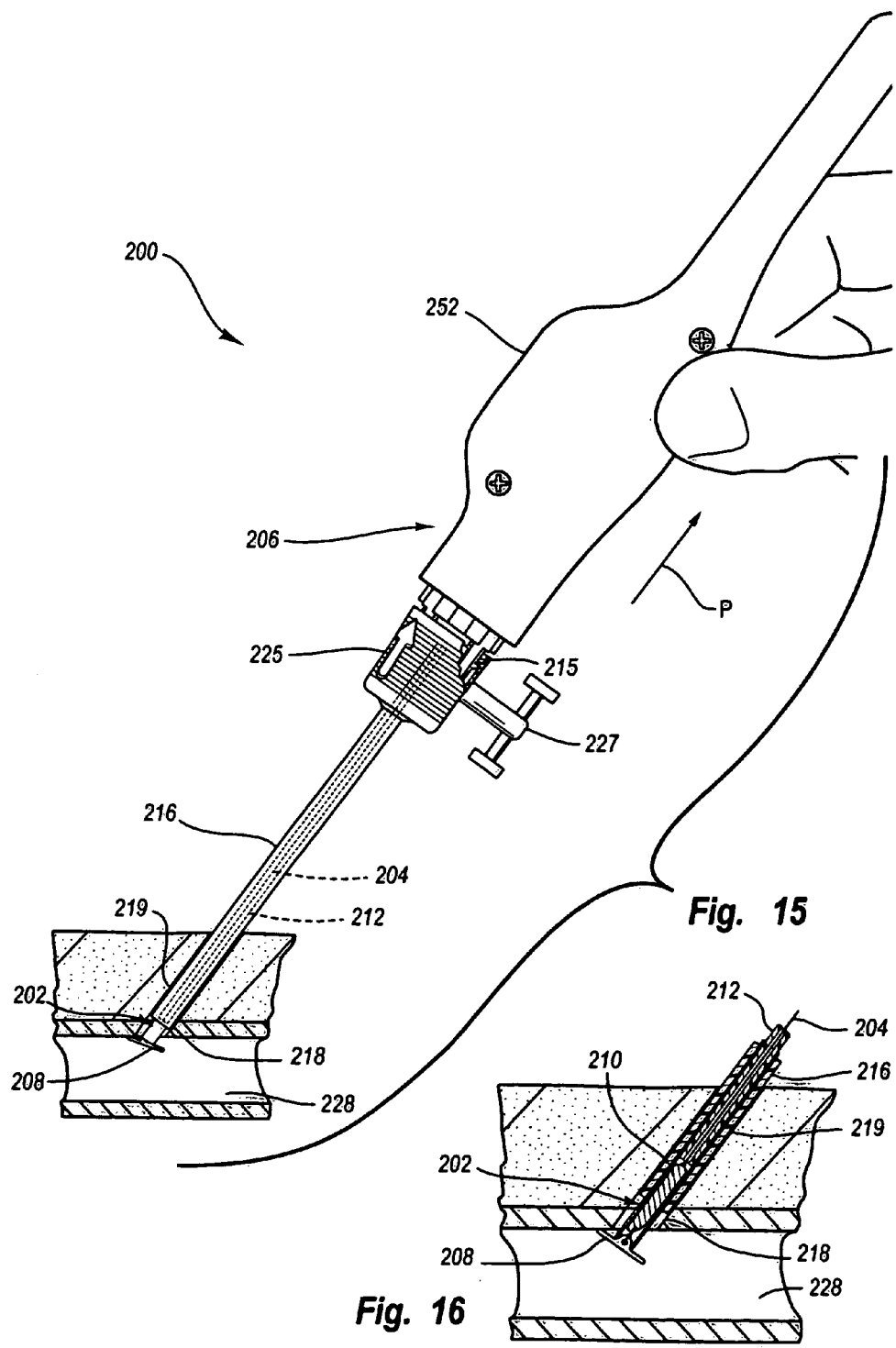
FIG. 15 is a side view of the vascular closure device and insertion sheath of FIG. 14 with the anchor member contacting a side wall of the tissue.
FIG. 16 is a detailed view of FIG. 15.

Referring to FIG. 14, the carrier tube 202 and anchor 208 are further advanced relative to the insertion sheath 216 until the anchor 208 is positioned entirely distally of a distal end of the insertion sheath 216. The distal portion 260 of the carrier tube 202 recoils in a radial direction to eliminate a recess feature 264 and return to an undeformed state. The anchor 208 rotates by contact with either a distal end surface of the carrier tube 202, or a distal end surface of the insertion sheath 216. In the illustrated example, the anchor 208 contacts the distal end surface of the carrier tube 202 and retains a rotated position shown in FIGS. 15 and 16 in which the anchor 208 may contact an inner side wall of the vessel 228 adjacent to the vessel puncture 218.

Figure 17:
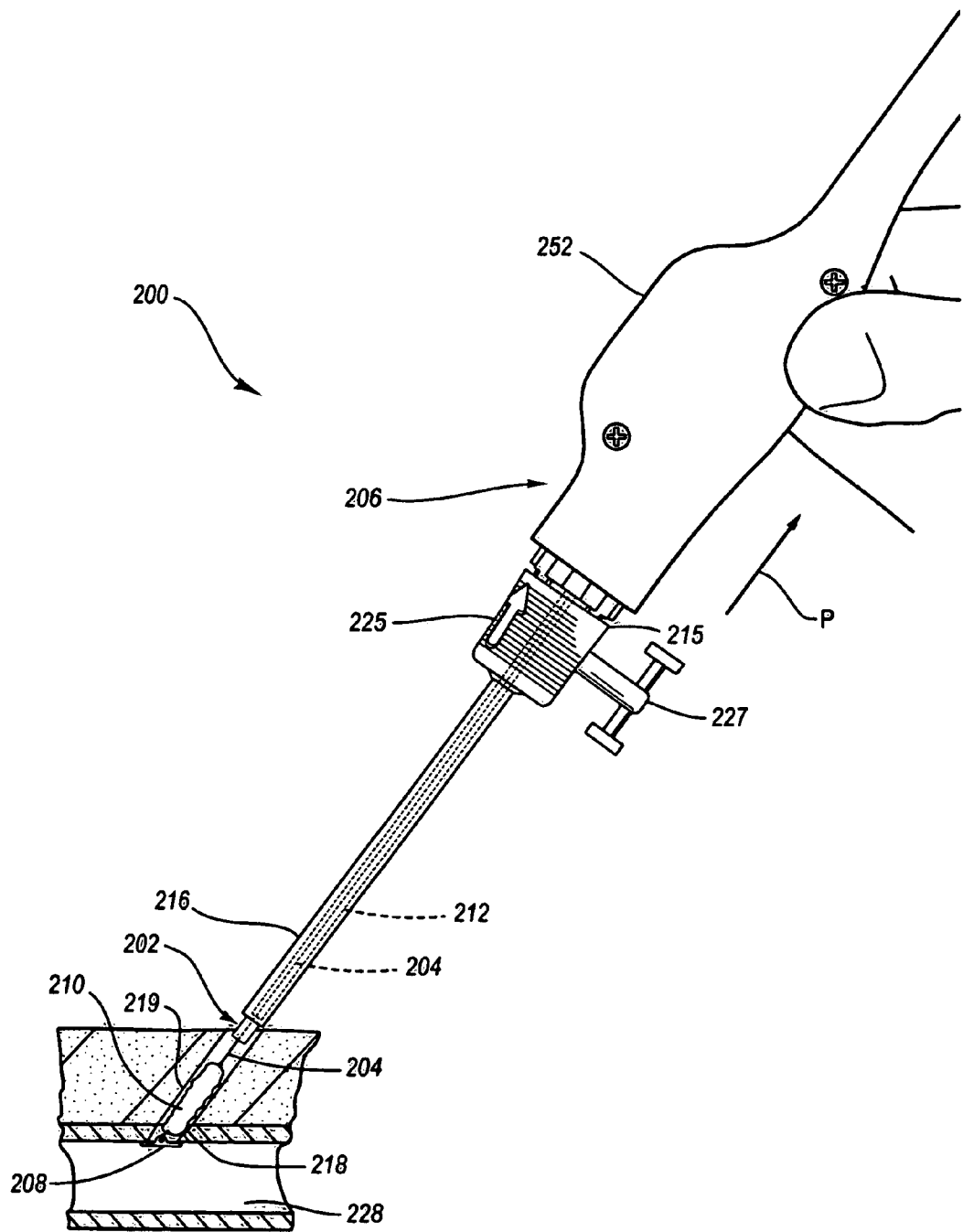
FIG. 17 is a side view of the vascular closure device and insertion sheath of FIG. 15 with a sealing pad disposed in the percutaneous incision adjacent to the tissue puncture.
Figure 18:
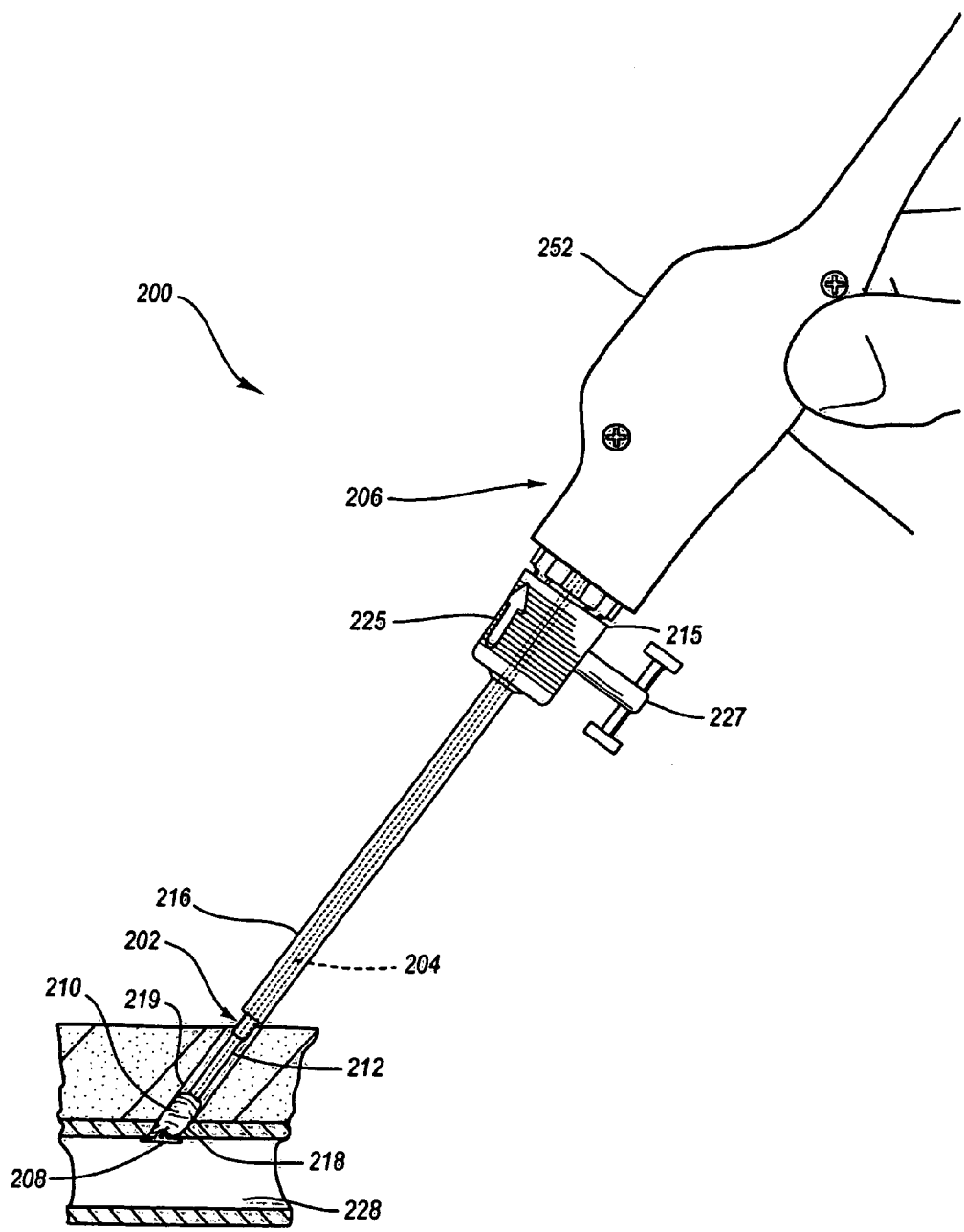
FIG. 18 is a side view of the vascular closure device and insertion sheath of FIG. 17 with the sealing pad compacted toward the anchor.

Referring now to FIG. 17, the carrier tube 202 and insertion sheath 216 are retracted in the proximal direction P to dispose the sealing pad 10 within the percutaneous incision 219 adjacent to the vessel puncture 218. A tamping assembly 230 (see FIG. 12) of the vascular closure device 200 is then activated to advance the compaction tube 212 in the distal direction D to compact the sealing pad 210 toward the anchor 208. The tamping assembly 230 may also concurrently cinch the sealing pad 210 and anchor 208 together with the suture 204.

After compaction of the sealing pad 210 is complete, the suture 204 is unwound to permit removal of the carrier tube 202 and sheath 216 from the percutaneous incision 219, and the suture 204 is manually cut to release the vascular closure device 200 and insertion sheath 216 from the sealing pad 210 and anchor 208. It may be possible in other arrangements to provide a compactionless sealing pad 210 that provides sealing of the vessel puncture 218 and percutaneous incision 219 without significant, if any, compaction of the sealing pad 210 towards the anchor 208. Further, in some arrangements it may be possible to automatically cut the suture using, for example, features of the vascular closure device 200. Many different types of vascular closure devices are possible which include manual, automatic, or combinations of manual and automatic tamping, cutting, and sealing pad positioning features that can implement the carrier tube configurations disclosed herein.

Figure 19:
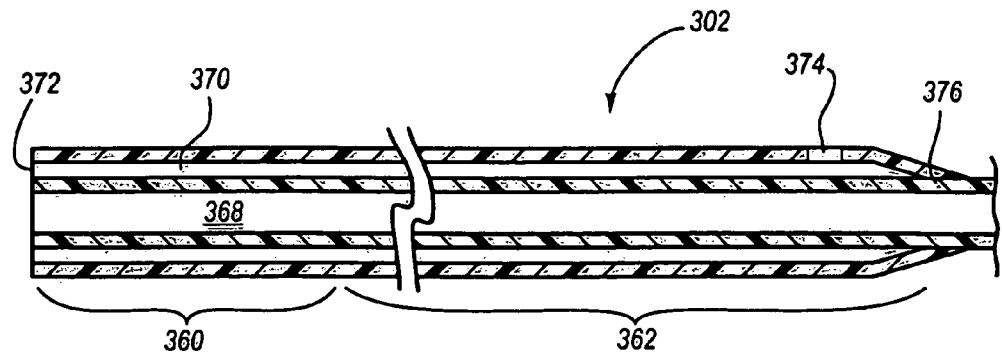
FIG. 19 is a cross-sectional side view of a portion of a carrier tube for use in the vascular closure devices disclosed herein.
Figure 20:
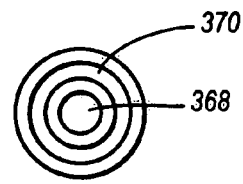
FIG. 20 is an end view of the carrier tube of FIG. 19.

The deformable distal end features of the carrier tubes disclosed herein may be used in combination with other carrier tube features such as, for example, blood flow indicating features. Referring to FIGS. 19 and 20, an example coaxially arranged carrier tube 302 is shown and described. The carrier tube 302 includes distal and proximal end portions 360, 362 that may have the same or similar features to the distal and proximal end portions of the carrier tube described above with reference to FIGS. 5-18. Carrier tube 302 may also include a first lumen 368 sized to retain, for example, a sealing pad and at least portions of a compaction device. A second blood flow lumen 370 is arranged coaxially with the first lumen 368. The blood flow lumen 370 has a distal opening 372 positioned at, for example, some location along the distal end portion at a distal end portion 360. A proximal outlet 374 is positioned at some location along the length of the carrier tube 302 proximal of the inlet 372. In at least some examples, the outlet 374 is positioned at a location proximal of a proximal end of the insertion sheath within which the carrier tube 302 is inserted during operation of the vascular closure device.

Carrier tube 302 may also include a proximal bond location 376 where the coaxially arranged tubes that define the carrier tube 302 are connected together. The proximal bond 376 may be formed using, for example, one of the bonding techniques described above related to connection of the distal and proximal portions of the carrier tube. For example, hot jaw, infrared (IR), radio frequency (RF), diode laser, and ultrasonic welding may be used to connect the coaxial tubes of the carrier tube 302 to create the proximal bond 376.

Figure 21:
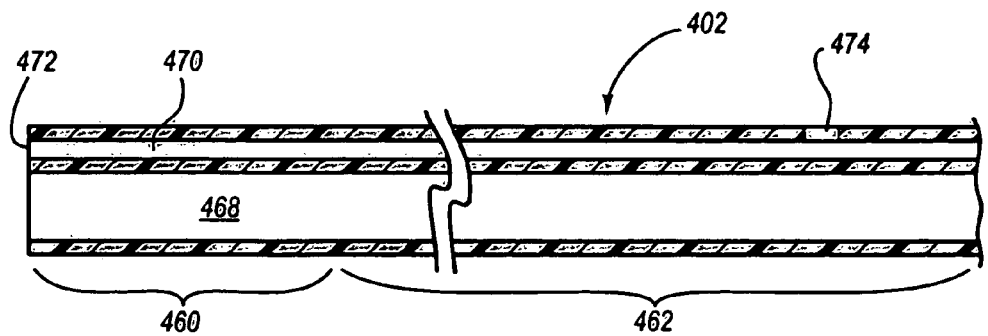
FIG. 21 is a cross-sectional side view of another example portion of a carrier tube for use with the vascular closure devices disclosed herein.
Figure 22:
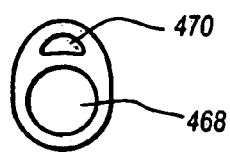
FIG. 22 is an end view of a carrier tube of FIG. 21.

Referring to FIGS. 21 and 22, another example carrier tube construction 402 is shown and described. The carrier tube 402 includes side-by-side arranged lumens 468, 470. A first lumen 468 is sized to receive, for example, a sealing pad and a compaction member. The lumen 470 may act as a blood flow lumen through which blood enters at a distal opening or inlet 472 and exits from a proximal outlet at opening 474. The outlet 474 is typically positioned proximal of the inlet 472. The location of the inlet 472 and outlet 474 may be any position along the length of the carrier tube 402. Typically, the inlet 472 is positioned along a distal portion 460 of the carrier tube 402 and the outlet 474 is positioned at some location along the proximal portion 462. The distal and proximal portions 460, 462 may have any of those features and capabilities described above with any of the proximal and distal portions of the carrier tubes described with reference to FIGS. 5-18.

The carrier tube 402 may be constructed as a single piece unit using, for example, extrusion methods and a polymeric material. In other arrangements, two separate tubular structures may be heat bonded together to provide the lumens 468, 470 in a side-by-side arrangement wherein the lumens 468, 470 are spaced apart in a radial direction.

The blood flow lumens 370, 470 described above with reference to FIGS. 19-22 may be particularly useful in providing an indicator to the operator that a certain portion (i.e., a distal end surface) of the carrier tube is positioned within the vessel. Typically, when the distal openings 372, 472 are exposed within the vessel, blood will flow through the lumens 370, 470 and exit out of the outlets 374, 474. The operator thus is able to receive a blood flow confirmation in addition to any visual indicators provided to confirm relative positions of the insertion sheath and vascular closure device that would indicate a location of certain features of the vascular closure device relative to the vessel.

The blood flow lumens 370, 470 have been shown and described herein in combination with deformable distal end features of a carrier tube. However, the blood flow lumens 370, 470, and variations thereof described above, may be implemented into any carrier tube design, including those carrier tube designs without deformable distal end features.

The preceding description has been presented only to illustrate and describe exemplary embodiments of the present disclosure. It is not intended to be exhaustive or to limit the invention to any precise form disclosed. Many modifications and variations are possible in light of the above teaching. It is intended that the scope of the invention be defined by the following claims.

What is claimed is:

1. A vascular closure device, comprising:
    a carrier tube defining a first lumen and comprising an insertion sheath having a distal end and being configured for insertion through a vessel puncture; a distal portion and a proximal portion, the distal portion having a different material composition from the proximal portion, the carrier tube being insertable through an insertion sheath;
    an anchor positioned outside of the carrier tube while the carrier tube is positioned inside the insertion sheath;
    a sealing pad positioned inside the first lumen;
    a suture coupling the sealing pad to the anchor.

2. The vascular closure device of claim 1, wherein the distal portion of the carrier tube has at least one of a greater flexibility, a greater compressibility, and a greater deformability than the proximal portion of the carrier tube.

3. The vascular closure device of claim 1, wherein the distal portion includes at least one of a thermoplastic polyurethane material, a thermoplastic polyethylene material, a hydrogel material, and a shape memory polymer.

4. The vascular closure device of claim 3, wherein the distal portion comprises a hydrogel material, wherein the hydrogel material is an electroactive polymer (EAP).

5. The vascular closure device of claim 1, wherein a portion of the anchor is arranged adjacent to a peripheral outer surface of the distal portion of the carrier tube.

6. The vascular closure device of claim 1, wherein the distal portion of the carrier tube is movable between a deformed position and a rest position, the deformed position defining a recess within which a portion of the anchor is positioned.

7. The vascular closure device of claim 6, wherein the distal portion maintains the deformed position while positioned in the insertion sheath and is configured to automatically move to the rest position after removal from the insertion sheath to limit return movement of the anchor into the insertion sheath.

8. The vascular closure device of claim 1, wherein the carrier tube defines a second lumen arranged coaxial with the first lumen, the second lumen being configured and arranged as a blood flow channel from the distal portion to the proximal portion of the carrier tube.

9. The vascular closure device of claim 1, wherein the carrier tube defines a second lumen arranged parallel with and radially spaced apart from the first lumen, the second lumen being configured and arranged as a blood flow channel from the distal portion to the proximal portion of the carrier tube.

10. The vascular closure device of claim 1, wherein the distal portion comprises a lubricious component.

11. The vascular closure system of claim 1, wherein the distal portion has a different material thickness than a material thickness of the proximal portion.

12. The vascular closure system of claim 1, wherein the distal portion has a different flexibility property than the proximal portion.

13. The vascular closure system of claim 1, wherein the distal portion includes a shape memory material.

14. The vascular closure system of claim 1, wherein the insertion sheath maintains a constant shape and size during use with the vascular closure device.

15. A vascular closure system, comprising:
an insertion sheath having a distal end and being configured for insertion through a vessel puncture;
a vascular closure device including:
a carrier tube having a proximal portion and a distal portion, the distal portion being elastically deformable to define a recess along an outer surface thereof, the carrier tube being positionable within the insertion sheath;
an anchor having at least a portion thereof positioned in the recess while the distal portion of the carrier tube is positioned in the insertion sheath;
a sealing pad positioned in the carrier tube and coupled to the anchor with a suture;
wherein when the distal portion of the carrier tube extends beyond the distal end of the insertion sheath, the distal portion automatically returns to an undeformed state to eliminate the recess.

16. The vascular closure system of claim 15, wherein the distal portion comprises a different material composition than the proximal portion.

17. The vascular closure system of claim 15, wherein the distal portion has a different material thickness than a material thickness of the proximal portion.

18. The vascular closure system of claim 15, wherein the distal portion has a different flexibility property than the proximal portion.

19. The vascular closure system of claim 15, wherein the distal portion includes a shape memory material.

20. The vascular closure system of claim 15, wherein the insertion sheath maintains a constant shape and size during use with the vascular closure device.

* * * * *